United States Patent
Rice et al.

(10) Patent No.: US 7,025,752 B2
(45) Date of Patent: Apr. 11, 2006

(54) REDUCED SLIPPAGE BALLOON CATHETER AND METHOD OF USING SAME

(75) Inventors: Cheryl Rice, San Diego, CA (US); Rosabel Chang, San Jose, CA (US); Jacky G. Duchamp, Campbell, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 601 days.

(21) Appl. No.: 10/288,783

(22) Filed: Nov. 6, 2002

(65) Prior Publication Data

US 2004/0087901 A1    May 6, 2004

(51) Int. Cl.
*A61M 5/32* (2006.01)
(52) U.S. Cl. .................................................. 604/265
(58) Field of Classification Search ............... 606/108, 606/192, 194, 195, 198; 604/96.01, 103.06, 604/172, 264, 265; 623/1.46, 1.11
See application file for complete search history.

(56) References Cited

U.S. PATENT DOCUMENTS

| | | |
|---|---|---|
| 4,459,317 A | 7/1984 | Lambert |
| 5,503,631 A | 4/1996 | Onishi et al. |
| 5,693,014 A | 12/1997 | Abele et al. |
| 6,261,630 B1 | 7/2001 | Nazarova et al. |
| 6,306,144 B1 | 10/2001 | Sydney et al. |
| 6,673,053 B1* | 1/2004 | Wang et al. ............... 604/265 |
| 6,866,649 B1* | 3/2005 | Ferrera et al. .......... 604/96.01 |
| 2002/0022849 A1 | 2/2002 | Sydney et al. |

FOREIGN PATENT DOCUMENTS

| | | |
|---|---|---|
| EP | 0 778 012 A2 | 6/1997 |
| WO | WO 94/27665 | 12/1994 |
| WO | WO 97/31674 | 9/1997 |
| WO | WO 00/67828 | 11/2000 |

* cited by examiner

*Primary Examiner*—Kevin T. Truong
(74) *Attorney, Agent, or Firm*—Fulwider Patton LLP

(57) ABSTRACT

A balloon catheter having a balloon with a reduced slippage lubricious coating, and a method of performing a medical procedure such as a balloon dilatation procedure in a patient's blood vessel. The second coating (i.e., the balloon coating) is lubricious to facilitate movement of the catheter in the patient's body lumen, yet has sufficiently low lubricity such that the slippage of the inflated balloon from a desired site within the blood vessel is reduced compared to a balloon coated with the first lubricious coating.

10 Claims, 2 Drawing Sheets

REDUCED SLIPPAGE BALLOON CATHETER AND METHOD OF USING SAME

BACKGROUND OF THE INVENTION

This invention generally relates to catheters, and particularly protective sheaths for intravascular catheters for such as balloon catheters used in percutaneous transluminal coronary angioplasty (PTCA) or for the delivery of stents.

In percutaneous transluminal coronary angioplasty (PTCA) procedures a guiding catheter is advanced in the patient's vasculature until the distal tip of the guiding catheter is seated in the ostium of a desired coronary artery. A guidewire is first advanced out of the distal end of the guiding catheter into the patient's coronary artery until the distal end of the guidewire crosses a lesion to be dilated. A dilatation catheter, having an inflatable balloon on the distal portion thereof, is advanced into the patient's coronary anatomy over the previously introduced guidewire until the balloon of the dilatation catheter is properly positioned across the lesion. Once properly positioned, the dilatation balloon is inflated with inflation fluid one or more times to a predetermined size at relatively high pressures so that the lesion is compressed against the arterial wall and the wall expanded to open up the vascular passageway. Generally, the inflated diameter of the balloon is approximately the same diameter as the native diameter of the body lumen being dilated so as to complete the dilatation but not overexpand the artery wall. After the balloon is finally deflated, blood flow resumes through the dilated artery and the dilatation catheter and the guidewire can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate of angioplasty alone and to strengthen the dilated area, physicians now normally implant an intravascular prosthesis, generally called a stent, inside the artery at the site of the lesion. Stents may also be used to repair vessels having an intimal flap or dissection or to generally strengthen a weakened section of a vessel or to maintain its patency. A tubular cover formed of synthetic or natural material may be present on an outer or inner surface of the stent. Stents are usually delivered to a desired location within a coronary artery in a contracted condition on a balloon of a catheter which is similar in many respects to a balloon angioplasty catheter, and expanded within the patient's artery to a larger diameter by expansion of the balloon. The balloon is deflated to remove the catheter and the stent left in place within the artery at the site of the dilated lesion. See for example, U.S. Pat. No. 5,507,768 (Lau et al.) and U.S. Pat. No. 5,458,615 (Klemm et al.), which are incorporated herein by reference.

An essential step in effectively performing a PTCA procedure is properly positioning the balloon catheter at a desired location within the coronary artery. To facilitate advancement of the catheter within the tortuous vasculature, conventional balloon catheters for angioplasty and stent delivery frequently have a lubricious coating on at least a portion of an outer surface of the catheter. However, one difficulty has been the tendency of the balloon having a lubricious coating thereon to slip out of position during inflation of the balloon. Accordingly, it would be a significant advance to provide a catheter balloon having improved balloon retention, and without inhibiting movement of the catheter within the vasculature.

SUMMARY OF THE INVENTION

This invention is directed to a balloon catheter having a balloon with a reduced slippage lubricious coating, and a method of performing a medical procedure such as a balloon dilatation procedure in a patient's blood vessel.

The balloon catheter of the invention generally includes an elongated shaft having a proximal end, a distal end, an inflation lumen, and a first lubricious coating with a first amount per unit area of lubricious material on at least a portion of the shaft, and a balloon on a distal shaft section having an interior in fluid communication with the inflation lumen, and a second lubricious coating on at least a portion of the balloon, the second lubricious coating having a second amount per unit area of lubricious material which is less than the first amount per unit area of lubricious material. In a presently preferred embodiment, the shaft includes a distal tip section, which in one embodiment is formed of a separate distal tip member, having at least a portion distal to the balloon and coated with the second lubricious coating. In one embodiment, the shaft comprises an outer tubular member defining the inflation lumen, and an inner tubular member defining a guidewire receiving lumen extending in at least a distal portion of the outer tubular member, and the first lubricious coating is on an outer surface of a proximal and a distal section of the outer tubular member defining an outer surface of the catheter. The second lubricious coating on the balloon preferably extends along the entire length of an outer surface of the balloon, although in alternative embodiments, the second lubricious coating may be on less than the entire outer surface of the balloon, and for example may be on intermittent portions of the balloon outer surface.

In one embodiment, the lubricious material of the first and second coating is a hydrophilic material, and in a presently preferred embodiment, is a polyethylene oxide based lubricious coating. However, a variety of suitable lubricious materials can be used including hydrophobic materials. In a presently preferred embodiment, the lubricious material of the first and second coatings is the same lubricious material, but, in accordance with the invention, is applied so that the balloon is coated with a smaller amount per unit area of the lubricious material, and thus a less lubricious coating, than at least the part of the shaft proximal thereto. The second coating (i.e., the balloon coating) is lubricious to facilitate movement of the catheter in the patient's body lumen, yet has sufficiently low lubricity such that the slippage of the inflated balloon from a desired site within the blood vessel is reduced compared to a balloon coated with the first lubricious coating. The coated balloon inflates into contact with, and remains at least partially in contact with a stenosed section of the blood vessel. Thus, the balloon catheter provides for improved dilatation of the desired region of the blood vessel by reducing the tendency of the lubriciously coated balloon to slip proximally or distally from the stenosed section of the blood vessel. The first lubricious coating on the balloon is relatively highly lubricious and thus facilitates movement of the catheter in the body lumen.

The second coating has a relatively small amount of lubricious material, to thereby provide a balloon surface which is more lubricious than a bare (non-coated) balloon, yet which has an insubstantial amount of slippage when inflated into contact with the blood vessel. Preferably, the second amount of lubricious material per unit area is not more than about 2.5% to about 3% of the first amount per unit area, and is most preferably about 1% to about 2.5% of the first amount per unit area. The coatings can be applied using a variety of suitable methods including wiping, spraying, and dipping solutions of the lubricious material onto the outer surface of at least a portion of the shaft and at least a portion of the balloon. The solutions on the catheter are typically cured to produce the lubricious coatings on the catheter. The cured lubricious coatings typically consist of the lubricious material and a matrix material. In a presently preferred embodiment, the first and second solutions which are applied to the catheter to form the first and second coatings, respectively, have an amount of lubricious material in the same proportion as in the cured coatings (i.e., the concentration of lubricious material in the second solution is not more than about 2.5% to about 3% of the concentration of lubricious material in the first solution). In a presently preferred embodiment, the second solution is prepared by diluting the first solution with additional solvent, with the absolute amount of lubricious material being about the same in the two solutions. As a result, after removal of the solvents during curing of the coatings on the balloon and shaft, the concentration of lubricious material (grams of lubricious material per gram of cured coating) of the second cured coating on the balloon is the about the same as the concentration of lubricious material of the first cured coating on the shaft. However, in a presently, preferred embodiment, approximately the same amount of solution is applied to the shaft as to the balloon, so that the resulting cured coatings on the shaft and the balloon have an amount (mass) of lubricious material per unit area ($gm/in^2$) in the same proportion as the amount of lubricious material in the two solutions (i.e., the solution of lubricious material applied to the balloon has a concentration of lubricious material which is not more than about 2.5% to about 3% of the concentration of lubricious material in the solution of lubricious material applied to the shaft, and the resulting mass of lubricious material per unit area in the cured second lubricious coating on the balloon is not more than about 2.5% to about 3% of the mass of lubricious material per unit area in the cured first lubricious coating on the shaft. However, it should be understood that there are a variety of ways of forming the coatings on the shaft and balloon with the desired relative amounts of lubricious material, including applying different amounts of lubricious solution, and applying lubricious solutions which do not have an amount of lubricious material in the same proportion as the amount of lubricious material in the resulting cured coatings on the shaft and the balloon.

The balloon coated with the second lubricious coating has a slip angle which is less than a slip angle of a bare (non-coated) balloon and greater than a slip angle of a balloon coated with the first lubricious coating. The slip angle is the critical angle at which the coated workpiece will slip out of position. A less lubricious surface has a higher slip angle than a more lubricious surface. A fixture for measuring the slip angle generally comprises a polymeric tube, and specifically a polyvinyl alcohol and dimethyl sulfoxide tube, which simulates a blood vessel, and a pusher with a weight which is on an outer surface of the tube and which can be oriented at different angles relative to the polymeric tube. The balloon is placed in the tube, with the angle at which the pusher contacts the tube simulating the angle of a lesion in a blood vessel, and the angle of the pusher is increased until the balloon slips longitudinally out of position during inflation of the balloon in the tube. Thus, the pusher squeezing on the balloon causes the balloon to slip longitudinally, and the higher the angle at which this slipping first occurs, the less likely the balloon is to slip out of position during inflation of the balloon in a patient's blood vessel (i.e., the relatively less lubricious the balloon outer surface). In a presently preferred embodiment, two measurements are made, namely, one with the pusher aligned at the balloon distal marker at the distal end of the balloon central working length, and another with the pusher aligned 1 mm proximal to the distal marker. Using this procedure the slip angle can be measured for various coatings to compare the effect of the relative lubricity of the various coatings on balloon slippage. The slip angle of the balloon coated with the second lubricious coating (i.e., the minimum angle of the pusher at which the balloon begins to slip in the polymeric tube) is about 4 to about 10 degrees, preferably about 8 to about 10 degrees, and the slip angle of a bare balloon is about 10 to about 15 degrees, preferably about 12 to about 15 degrees, and the slip angle of a balloon coated with the first lubricious coating is about 1 to about 7 degrees, preferably about 2 to about 6 degrees. It should be noted that at a relatively high angle of about 20 degrees the pusher begins to pinch the balloon and prevent the balloon from slipping longitudinally in the polymeric tube, so that a slip angle above 20 degrees cannot be measured with the slip angle fixture described above.

In a method of performing a medical procedure, a balloon catheter is advanced within a patient's blood vessel to a desired position at a stenosed section, the balloon catheter having a first lubricious coating with a first amount per unit area of lubricious material on at least a portion of the shaft and a second lubricious coating with a second smaller amount per unit area of lubricious material on at a least portion of the balloon, and the balloon is inflated so that the balloon working length contacts and dilates the stenosed section of the blood vessel. The coated surface of the balloon inflates into direct contact with the blood vessel wall/lesion, and the second coating limits or prevents the balloon from slipping longitudinally out of position. Preferably, the balloon catheter of the invention has a balloon which is at least about 40% less likely to slip out of position in a patient's body lumen during dilatation of a lesion than a balloon catheter having a balloon with the same lubricious coating as the shaft. In one embodiment, due to the limited amount of slippage of the balloon, a substantial portion of the inflated balloon working length remains in contact with the stenosed section of the blood vessel during the dilation. After the dilation, the balloon is deflated, and the catheter is repositioned or withdrawn from the blood vessel. The lubricious coatings on the catheter facilitate repositioning or withdrawing the deflated balloon catheter from the blood vessel.

The balloon catheter can be used for a variety of procedures including coronary or peripheral dilatation, drug delivery, intravascular prosthesis delivery and the like. The balloon catheter can have a variety of convention configurations including an over-the-wire type design, or a rapid exchange type design. Rapid exchange catheters generally comprise a distal guidewire port in a distal end of the catheter, a proximal guidewire port in a distal shaft section distal of the proximal end of the shaft and typically spaced a substantial distance from the proximal end of the catheter, and a short guidewire lumen extending between the proximal and distal guidewire ports in the distal section of the catheter.

The balloon catheter of the invention provides for improved dilatation of a patient's blood vessel, due to the first and second lubricious coatings on the shaft and balloon, respectively. The coated balloon surface has a sufficiently low lubricity to minimize the slippage of the inflated balloon out of position at the lesion during the dilatation, yet sufficiently high lubricity to facilitate movement of the catheter within the blood vessel. These and other advantages of the invention will become more apparent from the following detailed description of the invention and the accompanying exemplary drawings.

DETAILED DESCRIPTION OF THE INVENTION

Figure 1:
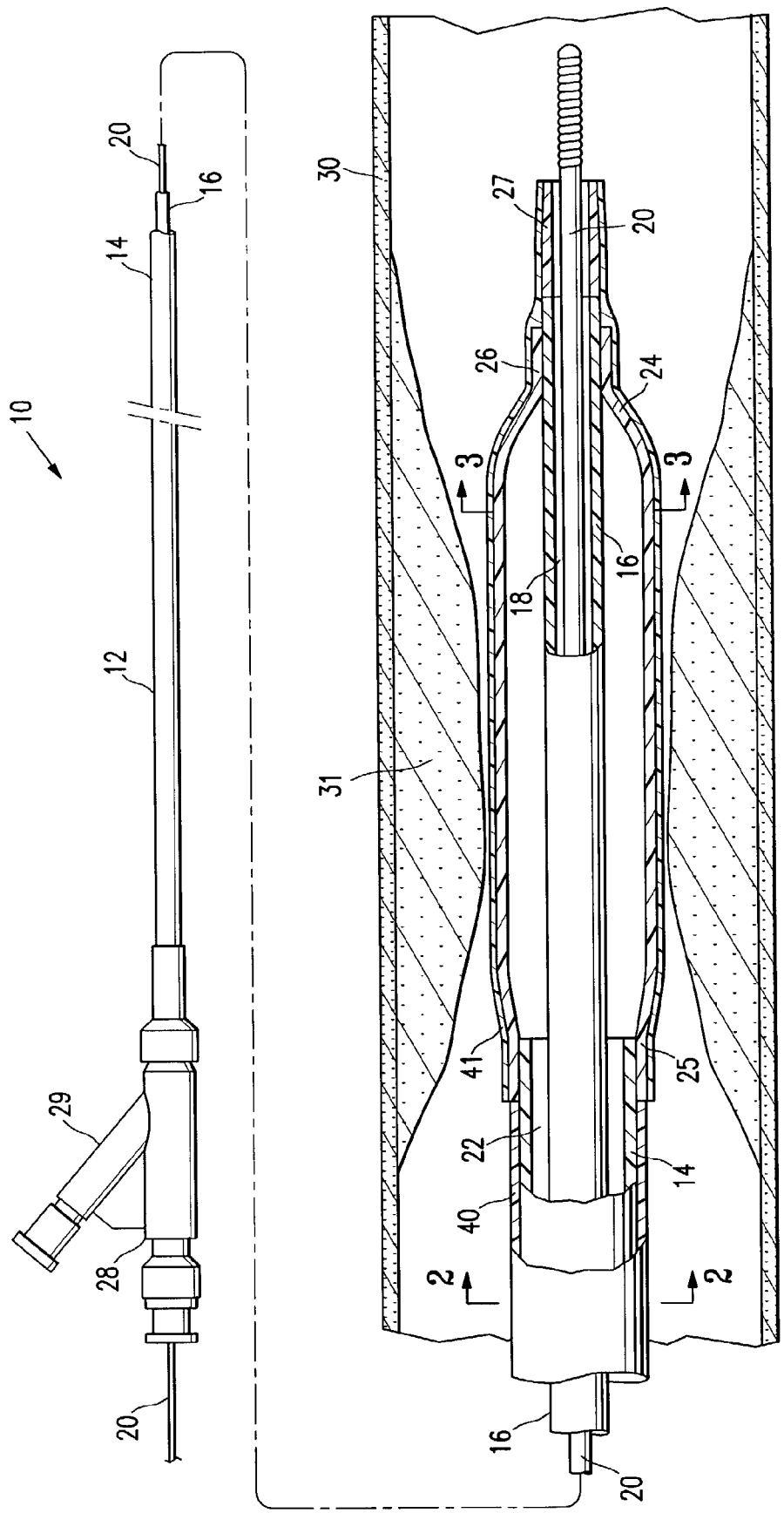
FIG. 1 is an elevational view, partially in section, of a balloon catheter embodying features of the invention, in a patient's body lumen.
Figure 2:
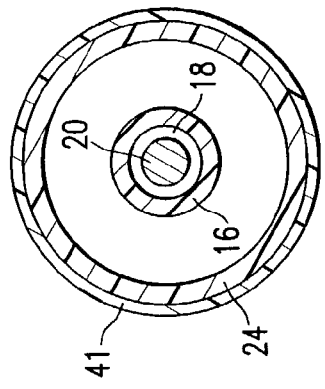
FIGS. 2 and 3 are transverse cross sectional views of the balloon catheter shown in FIG. 1, taken along lines 2—2 and 3—3, respectively.
Figure 3:
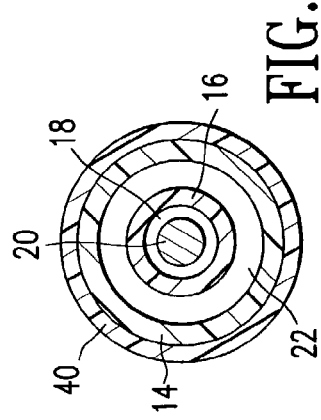

FIG. 1 illustrates an over-the-wire type balloon catheter 10 embodying features of the invention. Catheter 10 generally comprises an elongated catheter shaft 12 having an outer tubular member 14 and an inner tubular member 16. Inner tubular member 16 defines a guidewire lumen 18 configured to slidingly receive a guidewire 20, and the coaxial relationship between outer tubular member 14 and inner tubular member 16 defines annular inflation lumen 22, as best shown in FIG. 2 illustrating a transverse cross section view of the distal end of the catheter shown in FIG. 1, taken along line 2—2. An inflatable balloon 24 disposed on a distal section of catheter shaft 12 has an elongated cylindrical expandable working section, a proximal skirt section 25 sealingly secured to the distal end of outer tubular member 14 and a distal skirt section 26 sealingly secured to the distal end of inner tubular member 16, so that its interior is in fluid communication with inflation lumen 22. A distal tip 27 defining the distal end of the guidewire lumen 18 is located distal to the balloon 24. In the embodiment of FIG. 1, the distal tip 27 is a separate member butt joined to the distal end of the inner tubular member 16, with the butt joint located at the distal end of the balloon distal skirt section 26. However, in an alternative embodiment (not shown), the distal tip 27 and inner tubular member 16 are an integral, one-piece unit, so that the distal tip 27 is defined by the exposed outer surface of the distal end of the inner tubular member 16 distal to the distal end of the balloon 24. A variety of suitable distal tip configurations can be used as are conventionally known, including a distal tip having a proximal end surrounded by and bonded to another component of the catheter. An adapter 28 at the proximal end of catheter shaft 12 is configured to provide access to guidewire lumen 18, and to direct inflation fluid through arm 29 into inflation lumen 22. FIG. 1 illustrates the balloon 24 in a low profile tubular configuration prior to complete inflation. The distal end of catheter 10 may be advanced to a desired region of the patient's blood vessel 30 in a conventional manner, and balloon 24 inflated to expand the balloon 24 into contact with the lesion to dilate the stenosed section 31 of the blood vessel, and the balloon deflated and the catheter repositioned in the blood vessel or withdrawn therefrom. FIG. 3 illustrates a transverse cross section view of the distal end of the catheter shown in FIG. 1, taken along line 3—3.

The outer surface of the outer tubular member 14 has a first lubricious coating 40, and the outer surface of the balloon 24 has a second lubricious coating 41. In the embodiment of FIG. 1, the first lubricious coating 40 extends the entire length of the exposed outer surface of the outer tubular member 14 defining an outer surface of the catheter, and the second lubricious coating 41 extends the entire length of the balloon 24 and over the exposed outer surface of the distal tip 27. Thus, the portion of the outer tubular member 14 covered by and bonded to the proximal skirt section 25 of the balloon is not coated with the lubricious coating 40. The thickness of the coatings 40, 41 are exaggerated in the figures for ease of representation. In the embodiment of FIG. 1, the thicknesses of the cured coating 40 on the outer tubular member 14 is thicker than the thickness of the cured coating 41 on the balloon 24.

The second lubricious 41 coating has an amount per unit area of lubricious material which is less than the amount per unit area of lubricious material in the first lubricious coating 40, so that the first lubricious coating 40 on the outer tubular member 14 is more highly lubricious than the second lubricious coating 41 on the balloon 24. In a presently preferred embodiment, the first coating 40 is applied by applying a first solution of the lubricious material on the exposed outer surface of the outer tubular member 14 after the catheter has been assembled (i.e., the balloon secured to the inner and outer tubular members). Similarly, the second coating 41 is provided on the balloon by applying a second solution the lubricious material on the outer surface of the balloon 24 and the tip 27. Preferably, the concentration of lubricious material in the second solution is not more than about 2.5% to about 3% of the concentration in the first solution. In a presently preferred embodiment, the concentration of the first solution is about 1.0 to about 1.3 wt. % lubricious material, and the concentration of the second solution is about 0.01 to about 0.03 wt. % lubricious material. The solutions are cured, as for example by drying and/or ultraviolet (UV) curing, to form the coatings 40, 41 on the catheter. In one embodiment, the lubricious solutions comprise polyethylene oxide and trimethoylol propane triacrylate in benzophenone, hydrophenyl ketone and 1-hydroxycyclohexyl phenyl ketone.

The second lubricious coating is less lubricious than the first lubricious coating (i.e., it is less lubricious than a coating having 100% of the first amount of lubricious material), and is preferably less lubricious than a coating having as little as about 5% to about 10% of the first amount of lubricious material). Thus, the second lubricious coating has a slip angle which is greater than a slip angle of a lubricious coating having an amount of lubricious material which is about 5% to about 100% of the first amount. Surprisingly, a lubricious coating having about 5% to about 10% of the first amount of lubricious material had a slip angle about equal to the slip angle of the first lubricious coating, and thus was not significantly less lubricious than the first lubricious coating. For example, a 3.0 mm outer diameter balloon coated with a lubricious coating having about 5% of the first amount of lubricious material (i.e., coated with a solution of about 5 wt % of the first lubricious coating 40 solution) had a slip angle of about 6 to about 9 degrees, compared to a slip angle of about 4 to about 7 degrees for a similar 3.0 mm outer diameter balloon coated with the first lubricious coating 40.

While illustrated on the entire outer surface of the balloon 24, the second lubricious coating 41 may alternatively be on less than the entire outer surface of the balloon. Similarly, none or only part of the exposed outer surface of the tip 27 may be coated with the second lubricious coating 41, and may alternatively be coated in whole or in part with the first lubricious coating 40 or a different coating. In FIG. 1, the first lubricious coating 40 is on the entire exposed outer surface of the outer tubular member 14 (i.e., from the end of the adapter/strain relief member at the proximal end of the catheter, to the proximal shaft section 25 of the balloon 24). However, the first lubricious coating 40 may be on only part of the exposed outer surface of the outer tubular member, and is preferably on at least a distal section of the exposed outer surface of the outer tubular member (e.g., a distal section equal to about 18 to about 22% of the length of the outer tubular member 14). In a presently preferred embodiment, the proximal end of the coating 40 on the shaft is located distal to the proximal adapter 28. In the embodiment in which the balloon catheter is a rapid exchange type catheter having a guidewire proximal port located distal to the proximal end of the catheter, the first lubricious coating preferably extends along at least the exposed outer surface of the shaft distal to the guidewire proximal port, although it may alternatively also extend along the exposed outer surface of the tubular member forming the proximal shaft section proximal to the guidewire proximal port.

Although the coatings 40, 41 are illustrated with aligned ends at the proximal end of the balloon in the embodiment of FIG. 1 (i.e., the distal end of the coating 40 is at the proximal end of the coating 41), so that the coatings may abut one another, it should be understood that the coatings may alternatively overlap one another. For example, the first coating 40 may extend in part onto an outer surface of the balloon, or the second coating 41 may extend in part onto an outer surface of the outer tubular member, due to the manufacturing tolerances of the coating procedure. Thus, in one embodiment (not shown) a distal portion of the first coating 40 extends along at least a proximal section of the balloon and is subsequently covered by a proximal portion of the second coating 41, so that the proximal portion of the second coating 41 overlaps the distal portion of the first coating 40. However, in a presently preferred embodiment, the interface between the exposed outer surface of the first coating 40 and the exposed outer surface of the second coating 41 is located at (i.e., radially aligned with) the proximal end of the balloon, irrespective of whether the coatings are in an abutting or overlapping relation. Alternatively, the interface between the exposed outer surface of the first coating 40 and the exposed outer surface of the second coating 41 may be proximal or distal to the proximal end of the balloon.

Figure 4:
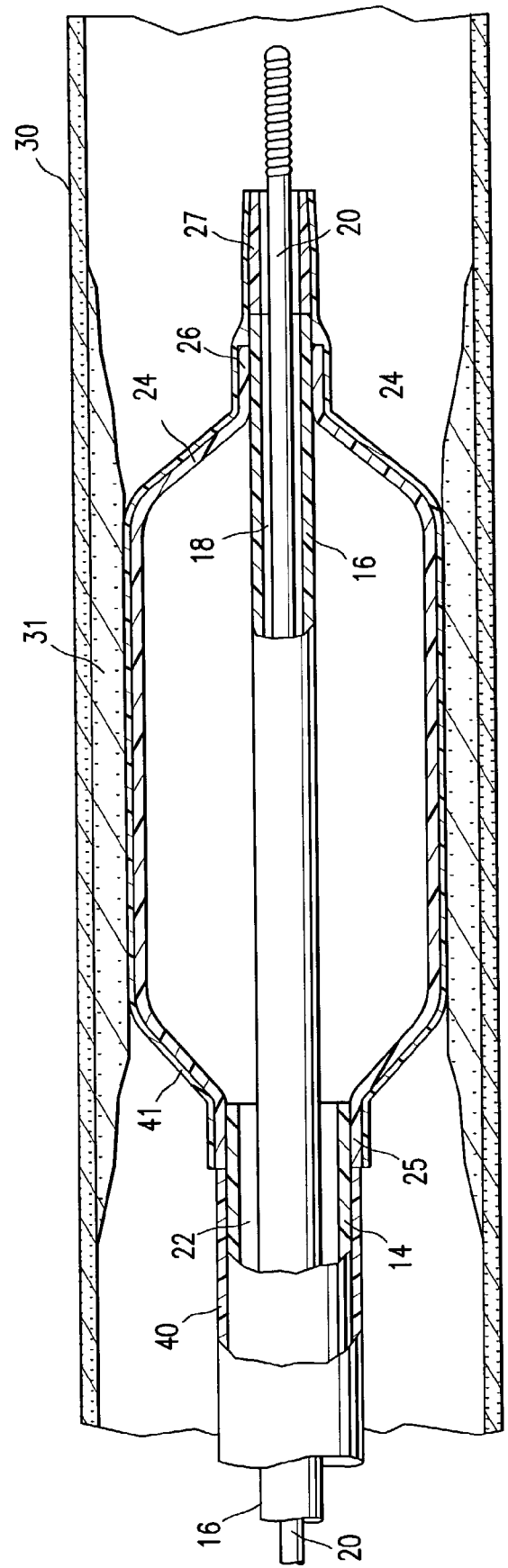
FIG. 4 is an enlarged, partially in section, view of the distal end of the balloon catheter shown in FIG. 1, with the balloon inflated during dilatation of the body lumen.

In a method of dilating the stenosed section 31, the balloon catheter 10 is advanced within the blood vessel 30 to position the balloon 24 at a desired position at the stenosed section 31. The balloon 24 is inflated so that the balloon working length contacts and dilates the stenosed section 31 of the blood vessel 30. FIG. 4 illustrates the inflated balloon in contact with and dilating the stenosed section 31. The inflated balloon in contact with the blood vessel/lesion preferably does not longitudinally slip, or at least has an insubstantial amount of slippage proximally or distally from the desired position at the stenosed section 31 during the dilatation. After the balloon is inflated one or more times to dilate the stenosed section 31 as is conventionally known, and the balloon is deflated a final time, to allow for repositioning or withdrawing the balloon catheter from the blood vessel. The lubricious coatings 40 and 41 remain on the catheter outer surface to facilitate removal or repositioning of the balloon catheter in the blood vessel.

To the extent not previously discussed herein, the various catheter components may be formed and joined by conventional materials and methods. For example, the outer and inner tubular members 14, 16 can be formed by conventional techniques, such as by extruding and necking materials found useful in intravascular catheters such a polyethylene, polyvinyl chloride, polyesters, polyamides, polyimides, polyurethanes, and composite materials. The length of the balloon catheter 10 is generally about 108 to about 200 centimeters, preferably about 137 to about 145 centimeters, and typically about 140 centimeters for PTCA. The outer tubular member 14 has an outer diameter (OD) of about 0.017 to about 0.036 inch (0.43–0.91 mm), and an inner diameter (ID) of about 0.012 to about 0.035 inch (0.30–0.89 mm). The inner tubular member 14 has an OD of about 0.017 to about 0.026 inch (0.43–0.66 mm), and an ID of about 0.015 to about 0.018 inch (0.38–0.46 mm) depending on the diameter of the guidewire to be used with the catheter. The balloon 24 is has a length of about 14 mm to about 46 mm, typically about 8 mm to about 40 mm, an inflated working diameter of about 1.5 mm to about 5.0 mm.

While the present invention has been described herein in terms of certain preferred embodiments, those skilled in the art will recognize that modifications and improvements may be made without departing form the scope of the invention. For example, although the embodiment illustrated in FIG. 1 has an outer and inner tubular member defining the inflation and guidewire lumens, respectively, the shaft may alternatively comprise a dual-lumen design as is conventionally known. Moreover, while individual features of one embodiment of the invention may be discussed or shown in the drawings of the one embodiment and not in other embodiments, it should be apparent that individual features of one embodiment may be combined with one or more features of another embodiment or features from a plurality of embodiments.

What is claimed is:

1. A balloon catheter, comprising:
   a) an elongated shaft having a proximal end, a distal end, and an inflation lumen, and having a first lubricious coating with a first amount per unit area of lubricious material on at least a portion of the shaft; and
   b) a balloon on a distal shaft section having an interior in fluid communication with the inflation lumen, and having a second lubricious coating with a second amount per unit area of lubricious material on at least a portion of the balloon, the second amount per unit area being not more than about 2.5% to about 3% of the first amount per unit area.

2. The balloon catheter of claim 1 wherein the shaft includes a distal tip section having at least a portion distal to the balloon and coated with the second lubricious coating.

3. The balloon catheter of claim 2 wherein the distal tip section is formed by a distal tip member secured to a distal end of a section of the shaft proximal thereto.

4. The balloon catheter of claim 1 wherein the shaft comprises an outer tubular member defining the inflation lumen and an inner tubular member defining a guidewire receiving lumen, and the first lubricious coating is on an outer surface of a proximal and a distal section of the outer tubular member.

5. The balloon catheter of claim 1 wherein the second lubricious coating extends along the entire length of an outer surface of the balloon.

6. The balloon catheter of claim 1 wherein the lubricious material of the first and second coating is the same.

7. The balloon catheter of claim 1 wherein the lubricious material of the first and second coating is polyethylene oxide.

8. The balloon catheter of claim 1 wherein the second amount per unit area of lubricious material is about 1% to about 2.5% of the first amount per unit area.

9. The balloon catheter of claim 1 wherein the balloon coated with the second lubricious coating has a slip angle which is less than a slip angle of a bare balloon and greater than a slip angle of a balloon coated with the first lubricious coating.

10. The balloon catheter of claim 1 wherein the balloon coated with the second lubricious coating has a slip angle which is greater than a slip angle of a balloon coated with a lubricious coating having an amount per unit area of the lubricious material which is about 5% to about 100% of the first amount per unit area.

* * * * *